United States Patent

Cannata et al.

[11] 4,423,244
[45] Dec. 27, 1983

[54] PROCESS FOR THE PREPARATION OF THE D-2-(6-METHOXY-2-NAPHTHYL)-PROPIONIC ACID

[75] Inventors: Vincenzo Cannata, Borgo Nuovo di Pontecchio Marconi; Giancarlo Tamerlani, Pontecchio Marconi, both of Italy

[73] Assignee: Alfa Chemicals Italiana S.p.A., Milan, Italy

[21] Appl. No.: 362,679

[22] Filed: Mar. 29, 1982

[30] Foreign Application Priority Data

Apr. 1, 1981 [IT] Italy ................................. 3385 A/81

[51] Int. Cl.³ .......................................... C07C 65/105
[52] U.S. Cl. ................................ 562/466; 260/501.17
[58] Field of Search ........................................ 562/466

[56] References Cited

U.S. PATENT DOCUMENTS 3,686,183  8/1972  Dyson ................................. 562/466
3,904,682  9/1978  Fried ................................. 562/466

*Primary Examiner*—Paul J. Killos
*Attorney, Agent, or Firm*—Bucknam and Archer

[57] ABSTRACT

A new process for the preparation of the d-2-(6-methoxy-2-naphthyl)-propionic acid of formula

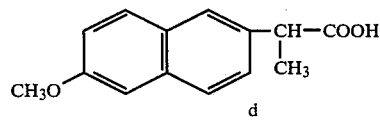

which comprises resolving a racemic mixture of the d- and l-2-(5-halo-6-methoxy-2-naphthyl)-propionic acids of formula

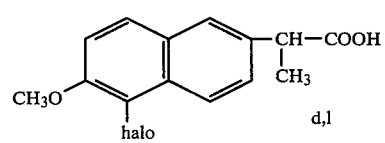

wherein halo stands for a halogen atom, recovering the d-isomer and subjecting this isomer to catalytic dehalogenation. Compound I is obtained in very high yields and with a high purity degree.

14 Claims, No Drawings

PROCESS FOR THE PREPARATION OF THE D-2-(6-METHOXY-2-NAPHTHYL)-PROPIONIC ACID

BACKGROUND OF THE INVENTION

The compound d-2-(6-methoxy-2-naphthyl)-propionic acid (naproxen, International Non-proprietary Name) is known from the literature for its excellent antiinflammatory properties. It was first described in U.S. Pat. No. 3,904,682. Several methods for its preparations are known which contemplate the synthesis of a racemic mixture of the d- and l-2-(6-methoxy-2-naphthyl) propionic acids (see for instance U.S. Pat. Nos. 3,658,863; 3,658,858; 3,663,584 and 3,694,770) which is subsequently resolved into the two optically active antipodes through formation of salts with optically active organic bases (see e.g. French publication No. 2,035,846 and U.S. Pat. No. 3,683,015). On the other hand, few methods are known, which deal with the synthesis of racemic mixtures of the d- and l-2-(5-halo-6-methoxy-2-naphthyl)-propionic acids, their resolution into the optically active antipodes and the final dehalogenation of the d-isomer to the desired end product. British Pat. Nos. 1,274,271; 1,274,272 and 1,274,273 describe for instance the synthesis of compound II as a racemic mixture but no example is given as to the resolution of said mixture into the optically active antipodes and to the dehalogenation of d-isomer either.

SUMMARY OF THE INVENTION

The present invention refers to a new process for preparing the d-2-(6-methoxy-2-naphthyl)-propionic acid of formula

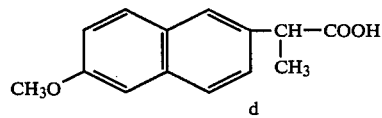

The process which is the object of the invention may schematically be represented as follows

SCHEME

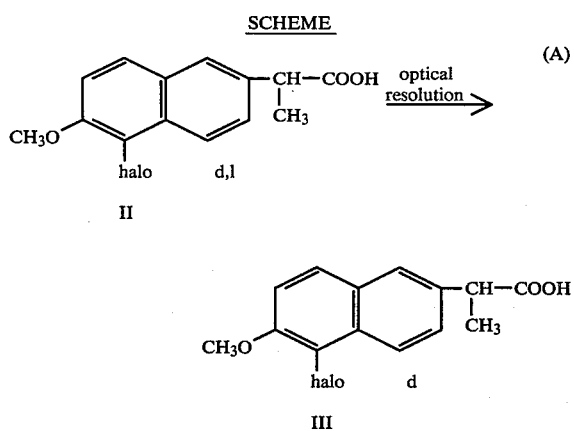

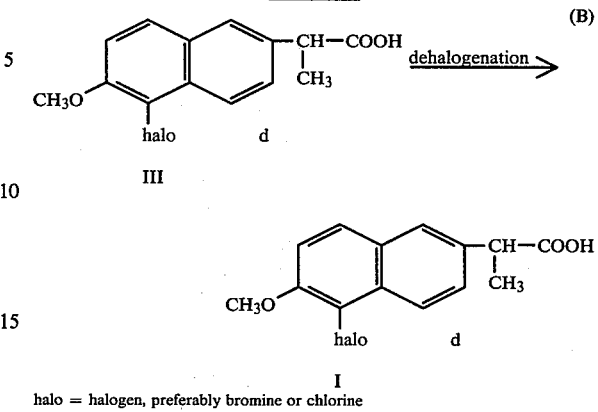

halo = halogen, preferably bromine or chlorine

According to step A, the optical resolution of the racemic mixture of 2-(5-halo-6-methoxy-2-naphthyl)-propionic acids is performed via the formation of the salts of the two isomers with optically active organic bases, taking advantage from the different solubilities of said salts in predetermined solvent systems.

Several optically active organic bases are known from the literature which prove to act more or less satisfactorily in resolving mixtures of the d- and l-2-(6-methoxy-2-naphthyl)-propionic acids into the corresponding optically antipodes. As an example, alkaloids like cinchonidine or other bases like alpha phenyl-ethyl-amine or dehydroabietylamine have extensively been used in such operations, but concrete examples of optical resolutions of mixtures of the d- and l-2-(5-halo-6-methoxy-2-naphthyl)-propionic acids have never been reported in the literature.

We have surprisingly found that, in order to obtain the desired d-2-(5-halo-6-methoxy-2-naphthyl)-propionic acid of formula III above with high yields and optical purity, quite peculiar conditions are needed, both with reference to the resolving agent and with reference to the solvent to be employed. As a matter of fact, an excellent separation is achieved by using N-methyl-D-glucamine as the resolving agent and a solvent system comprising toluene and methanol in different volumetric ratios.

In the actual practice, the optical resolution according to step A of the above scheme is carried out by dissolving or suspending in a solvent system formed by a mixture of toluene and methanol, preferably in the volumetric ratios toluene/methanol=4/1 or 3/1, a molar proportion of a substantially racemic mixture of d- and l-2-(5-halo-6-methoxy-2-naphthyl)-propionic acids, preferably the d- and l-2-(5-bromo-6-methoxy-2-naphthyl)-propionic acids, a half molar proportion or a slight excess over said amount, of N-methyl-D-glucamine, and an optically inactive organic or inorganic base such as, for instance, triethylamine or sodium or potassium hydroxide. The so obtained reaction mixture is stirred at substantially room temperature until a clear solution is obtained, then it is seeded with a small amount of a previously formed N-methyl-D-glucamine salt of the d-2-(5-halo-6-methoxy-2-naphthyl)-propionic acid, preferably the salt of the d-2-(5-bromo-6-methoxy-2-naphthyl)-propionic acid, in order to favor the precipitation of the desired d-isomer (as the N-methylD-glucamine salt) of formula III. This is advantageously obtained also by heating the dense suspension, which forms after seeding, at a temperature between about 40 and about 65° C., preferably at 55° C., and allowing the resulting solution to cool to about room temperature.

The obtained precipitate which, as stated above, is the N-methyl-D-glucamine salt of the d-2-(5-halo-6-methoxy-2-naphthyl)-propionic acid, preferably the salt of the d-2-(5-bromo-6-methoxy-2-naphthyl)-propionic acid, is then treated in a manner known per se, as an example with a strong mineral acid at room temperature, to give the desired substance of formula III wherein halo preferably represents a bromine atom.

The yield of this step is generally higher than 90% (calculated over the molar amount of d-isomer present in the starting mixture), being the obtained d-isomer practically free from the l-isomer. As a matter of fact, the d-isomer of formula III may undergo the dehalogenation reaction as per step B of the above scheme without being subjected to any further purification by recrystallization or analogous procedures.

Step B of the above reaction Scheme is carried out by treating a molar proportion of the d-2-(5-halo-6-methoxy-2-naphthyl)-propionic acid, preferably the 5-bromo compound, with a suitable hydrogenation system in order to removed the halogenation at the 5-position. These hydrogenation systems may be of various nature. As an example, a suitable hydrogenation system is represented by a hydrogenation catalyst such as, for instance, palladium charcoal or finely divided platinum dioxide alone or in admixture with a mixed metal hydride, as an example sodium borohydride. Other hydrogenation systems which have given satisfactory results comprise a mixture in various ratios of a mixed metal hydride and a salt of transition metal e.g., sodium borohydride and copper sulfate pentahydrate, sodium borohydride and nickel sulfate, sodium borohydride and cobalt sulfate and analogs. Another suitable hydrogenation system is represented by Devarda's alloy ie., an alloy containing 50 parts by weight of copper, 45 parts by weight of aluminum and 5 parts by weight of zinc, in the presence of a mixed metal hydride.

A further suitable hydrogenation system, which has proven to give the best results both in terms of final yields of the desired product and in terms of ease the reaction runs, is represented by a nickel/aluminum alloy, generally in a 50/50 (by weight) ratio, and hydrazine hydrate, or Ni/Raney and hydrazine hydrate, in various ratios.

In the actual practice, the dehalogenation reaction (step B of the above scheme) is carried out by contacting, under alkaline conditions, an amount of the d-2-(5-halo-6-methoxy-2-naphthyl)-propionic acid and, preferably, the d-2-(5-bromo-6-methoxy-2-naphthyl)-propionic acid, with a suitable amount of one of the above seen hydrogenation systems. Generally, said amount is selected in such a way so as to provide a complete replacement of the halogen atom at the 5-position of the compound of formula III above by a hydrogen atom. The reaction is carried out at a temperature comprised between about room temperature and about 100° C., but it has been found that a lower temperature interval, comprised between about room temperature and about 50° C., may be more conveniently applied when a 50/50 (by weight) nikel/aluminum alloy and hydrazine hydrate, or Ni/Raney and hydrazine hydrate are used as the hydrogenation systems. A time interval comprised between about 1 and about 4 hours is in general sufficient to complete the reaction.

Step B runs practivally with quantitative yields and the obtained final product ie., d-2-(6-methoxy-2-naphthyl)-propionic acid displays a specific rotatory power which is absolutely in agreement with the standards as set forth in the 1978 Addendum to the British Pharmacopoeia of 1973. Considering that the also yields of step A are never lower than 90% (calculated over the amount of the d-isomer present in the starting dl-misture) it derives that, the present invention provides a novel and useful method for preparing a valuable pharmaceutical compound, namely the d-2-(6-methoxy-2-naphthyl)-propionic acid. Finally, it must be pointed out that the above illustrated dehalogenation procedure can advantageously be carried out, under the same reaction conditions, by starting from a substantially racemic mixture of the d- and l-2-(5-halo-6-methoxy-2-naphthyl)-propionic acids. The so obtained mixture of the d- and l-2-(6-methoxy-2-naphthyl)-propionic acids may then be resolved into the corresponding optically active antipodes according to the method described in the Italian Application 3492 A/80 filed on July 30, 1980. According to this method, a solution of a mixture of the d- and l-2-(6-methoxy-2-naphthyl)-propionic acids and an optically active organic base, as an example cinchonidine, is prepared by dissolving the substances in an organic solvent selected from formamide, mono- and dimethylformamide, mono- and diethylformamide, mono- and dimethylacetamide at a temperature comprised between about 70° and about 90° C. The so obtained solution is slowly cooled and, at a predetermined temperature, is seeded with a small amount of the salt of the d-2-(6-methoxy-2-naphthyl)-propionic acid with the optically active organic base, said salt containing an amount by weight of the employed reaction solvent varying from about 9.5% and 14%. A precipitate forms, essentially consisting of the salt of the d-isomer with the optically active organic base, said salt still containing an amount of the employed reaction solvent varying from the above percent limits, from which the d-2-(6-methoxy-2-naphthyl)-propionic acid is obtained through conventional procedures in practically pure forms.

The starting compound of formula II namely d,l-2-(5-halo-6-methoxy-2-naphthyl)-propionic acids can be prepared according to various procedures. One of these comprises a multistep way which starts from 1-halo-2-methoxy-naphthalene of formula

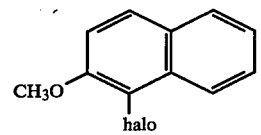

IV wherein halo represents a halogen atom, and runs through the following reaction scheme

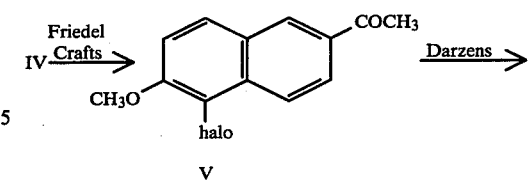

-continued

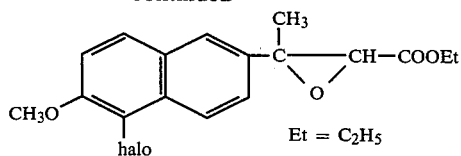

VI

VI $\xrightarrow{\text{(1) hydrolysis}}_{\text{(2) decarboxylation}}$

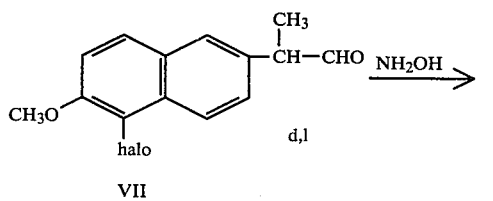

VII

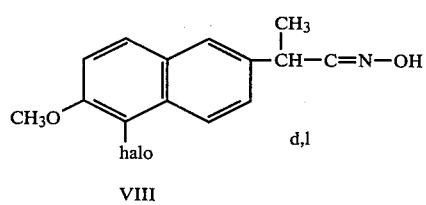

VIII

VIII $\xrightarrow{\text{OH}^-/\text{ethylene glycol}}$

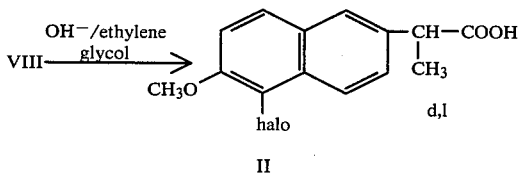

II

Thus, according to the above scheme, compound IV is reacted with a molar excess of acetyl chloride at a temperature comprised between about 0° and 10° C. in the presence of a halogenated hydrocarbon as the reaction solvent. These are typical Friedel-Crafts reaction conditions, though, advantageously, no nitrobenzene is employed as the reaction solvent. Furthermore, higher yields of the acetylated compound are observed. The so obtained 2-acetyl-5-halo-6-methoxy-naphthalene is transformed into compound VI through a Darzens' reaction which is first hydrolysed at room temperature for about 46 hours by means of an aqueous solution of an alkali metal hydroxide and subsequently decarboxylated to compound VII ie., d,l-2-(5-halo-6-methoxy-2-naphthyl)-propionaldehyde. The subsequent steps contemplate the formation of the oxime of formula VIII by treating the aldehyde of formula VII with hydroxylamine hydrochloride and the subsequent treatment of the oxime by means of a strong alkali agent such as, for instance, potassium hydroxide in the presence of ethylene glycol at a temperature varying from about 100° and about 140° C., for a period of time comprised between about 5 and about 8 hours. The yields of this multi-step procedure are practically quantitative. Another useful method for preparing the starting compound d,l-2-(5-halo-6-methoxy-2-naphthyl)-propionic acid comprises the hydrolysis under mild alkaline conditions of a compound of formula

IX namely d,l-2-(5-halo-6-methoxy)-2-naphthyl)-propionic acid β-halo′-ethyl ester, wherein halo and halo′ each independently represent a halogen atom. Compound IX is in turn prepared as described in European laid open application 35305. Other obvious methods for preparing the starting compound of formula II are intended to fall within the scopes of the present invention.

The following examples are provided for with the purpose of better illustrating the invention.

EXAMPLE 1

Preparation of the starting compound of formula II wherein halo is a bromine atom, namely d,l-2-(5-bromo-6-methoxy-2-naphthyl)-propionic acid (A) 2-Acetyl-5-bromo-6-methoxy-naphthalene (Compound V)

A suspension of 43 g of anhydrous $AlCl_3$ and 24.6 g (0.313 mole) of acetyl chloride in 200 ml of 1,2-dichloroethane at 10° C. was cooled to 0° C. and added dropwise under stirring with a solution of 59.25 g (0.250 mole) of 1-bromo-2-methoxy-naphthalene in 150 ml of 1,2-dichloroethane. The resulting solution was stirred for 15 minutes then poured into a cold solution of 300 ml of water and 100 ml of 2 N hydrochloric acid. The organic phase was separated, washed first with 100 ml of 1 N hydrochloric acid and then with 100 ml of water, dried under vacuum and the obtained residue was crystallized from 2-butanol. Yield 68.11 g (98%).

(B) d,l-5-Bromo-6-methoxy-2-naphthyl-propionaldehyde-(Compound VIII)

A mixture of sodium-2-butoxide (prepared from 9.28 g of sodium in 164 ml of 2-butanol) and 120 ml of toluene, kept at 10° C., was added with 55.8 g (0.2 mole) of the compound prepared under (A) and 42.4 ml of ethyl chloroacetate. The resulting mixture was stirred for 3 hours at 10° C., then 200 ml of water were added, the organic layer was separated and added under vigorous stirring with a solution of 45 g of 85% potassium hydroxide. After stirring for 5 hours at room temperature, a solid precipitate was obtained, which was filtered, washed with 100 ml of a 50/50 (v/v) toluene/2-butanol mixture and suspended in 200 ml of water. The aqueous suspension was heated 1 hour at 100° C., then cooled to room temperature whereby 57 g (almost quantitative yield) of compound VII were obtained.

(C) d,l-2-(5-Bromo-6-methoxy-2-naphthyl)-propionaldoxime-(Compound VIII)

49.8 Grams (0.170 mole) of the aldehyde VII were dissolved at room temperature in 100 ml of water and 100 ml of chloroform, then the resulting solution was added with 13.9 g of hydroxylamine hydrochloride in 50 ml of water, keeping the pH of the reaction between 6 and 7 by means of an aqueous solution of sodium carbonate. The resulting mixture was stirred for 30 minutes, whereby the title compound precipitated and was recovered by filtration. Upon concentration of the chloroformic mother liquors a further crop of title compound was collected. Yield 50.25 g (96%).

(D) d,l-2-(5-Bromo-6-methoxy-2-naphthyl)-propionic acid (Compound II)

A solution of 22.3 g of 85% potassium hydroxide in 55 ml of ethylene glycol was heated to 70° and was subsequently added with 45 g (0.146 mole) of the oxime prepared under C). The solution was then heated for 7 hours at 120° C. cooled to 90° C. and added with 450 ml of water. After extracting with 300 ml (2×150 ml) of methylene chloride, the aqueous phase was first heated to 90° C. and then brought to pH 4 by means of acetic acid. The obtained suspension was cooled to 25° C., filtered and the obtained solid abundantly washed with water and dried. Yield 45 g (98%) of d,l-2-(5-bromo-6-methoxy-2-naphthyl)-propionic acid.

EXAMPLE 2

Preparation of the starting compound of formula II wherein halo is a bromine atom, namely d,l-2-(5-bromo-6-methoxy-2-naphthyl)-propionic acid.

37.4 Grams (0.0903 mole) of d,l-2-(5-bromo-6-methoxy-2-naphthyl)-propionic acid 2-bromoethyl ester were suspended in 100 ml of methanol and 27.5 ml of water, the resulting suspension was added with 12.5 g of 90% potassium hyroxide and the whole was heated to 30° C. The mixture was vigorously stirred for 2 hours, then it was concentrated to small volume and taken up with 100 ml of water. The aqueous solution was washed with 150 ml of 1,2-dichloroethane then the pH value was adjusted to about 2 by adding concentrated hydrochloric acid at 50° C. After cooling to room temperature, the obtained precipitate was recovered by filtration, washed with water and dried. Yield: 27.3 g (98%) of the title compound.

EXAMPLE 3 d-2-(5-Bromo-6-methoxy-2-naphthyl)-propionic acid.

In a flask containing 360 ml of toluene, 90 ml of methanol and 26 ml of triethylamine, 116 g (0.376 mole) of d,1-2-(5-bromo-6-methoxy-2-naphthyl)-propionic and 36.5 g (0.186 mole) of N-methyl-D-glucamine were added at room temperature under stirring. The so obtained clear solution was then seeded with 0.5 g of the N-methyl-D-glucamine salt of the d-2-(5-bromo-6-methoxy-2-naphthyl)-propionic acid and, after 30 minutes a dense suspension formed. This suspension was heated to 55° C. and slowly cooled to 20° C., then it was filtered and the obtained solid was washed with 180 ml of a mixture 80/20 (v/v) of toluene and methanol.

The wet solid was dissolved in 500 ml of water and 600 ml of ethyl acetate, the pH of the solution was adjusted to 3 by means of concentrated hydrochloric acid, then the organic layer was washed with water and subsequently concentrated to dryness in vacuo. Yield 56.26 g (97% of theoretical) of d-2-(5-bromo-6-methoxy-2-naphthyl)-propionic acid.

$[\alpha]_{578}^{20} = +47.5°(C=0.5\%$ in $CHCl_3)$

EXAMPLE 4 d-2-(6-Methoxy-2-naphthyl)-propionic acid

A solution of 8 g of sodium hydroxide in 150 ml of water was added with 33.5 g (0.109 mole) of d-2-(5-bromo-6-methoxy-2-naphthyl)-propionic acid and 2 g of 5% palladium/charcoal. The reaction temperature was brought to 50° C., then a solution of 3 g of sodium borohydride in 30 ml of slightly alkaline water was added dropwise along 1 hour. After stirring for 15 minutes and cooled to 30° C., the catalyst was removed by filtration on Dicalite ® and the filtrate was added with 400 ml of ethyl acetate. The pH of the solution was brought to 3 by means of concentrated hydrochloric acid, the organic phase was separated, washed with water until neutrality and dried under vacuum. Yield 23.7 g (95% of theoretical) of d-2-(6-methoxy-2-naphthyl)-propionic acid.

$[\alpha]_D^{20} = +65.5°(C=1\%$ in $CHCl_3)$. M.p.=154°-55° C.

EXAMPLE 5 d-2-(6-Methoxy-2-naphthyl)-propionic acid

A solution of 2.5 g of copper sulfate pentahydrate, 12.5 g of 90% potassium hydroxide and 30.9 g (0.1 mole) of d-2-(5-bromo-6-methoxy-2-naphthyl)-propionic acid in 150 ml of water was first added with 1 g of charcoal and then, dropwise under stirring, with a solution of 3.8 g of sodium borohydride in 40 ml of slightly alkaline water. During the addition of the first third of said sodium borohydride solution, the temperature of the reaction mixture was gradually raised to 80° C., further 3.1 g of 90% potassium hydroxide were then added and the removing sodium borohydride solution was added in about two hours at the same temperature. After the addition was terminated, the reaction mixture was stirred for further 30 minutes, cooled to 30° C. and the catalyst was filtered off. The obtained filtrate was heated to 50° C., the pH was adjusted to 2 by means of concentrated hydrochloric acid, the solution was cooled to 20° C. whereby a solid formed, which was recovered by filtration, washed with water until neutrality and dried. Yield 22.4 g (97% of theoretical); $[\alpha]_D^{20} = +66°(C=1\%$ in $CHCl_3)$. M.p.=154°-55° C.

EXAMPLE 6 d-2-(6-Methoxy-2-naphthyl)-propionic acid

A mixture of 25 ml of a 40% aqueous solution (w/v) of sodium hydroxide and 150 ml of water was heated to 40° C. and added with 30.9 g (0.1 mole) of d-2-(5-bromo-6-methoxy-2-naphthyl)-propionic acid. After 5 minutes a clear solution is obtained which under a nitrogen atmosphere, was added with 1.2 g of a 50water suspension of Ni/Raney. The reaction temperature was brought to 50° C., then a solution of 4 ml of 100% hydrazine hydrate in 40 ml of water was added dropwise in about 90 minutes. After cooling and filtering off the catalyst, the filtrate was added with 150 ml of water, the resulting solution was heated to 80° C. and the pH adjusted to 2 by means of concentrated hydrochloric acid. Upon cooling to room temperature, a precipitate forms which was recovered by filtration, washed with water to neutrality and dried. Yield 22.5 g (98% of theoretical).

$[\alpha]_D^{20} = +68.4°(C=1\%$ in $CHCl_3)$. M.p.155°-56° C.

EXAMPLE 7 d-2-(6-Methoxy-2-naphthyl)-propionic acid 11.4 Liters of water, 1.7 Kilograms of an aqueous 40% solution (w/v) ov sodium hydroxide and 1.560 Kilograms of d-2-(5-bromo-6-methoxy-2-naphthyl)-propionic acid were poured into a 34 liters tank and the resulting solution was heated to 50° C. under nitrogen atmosphere and added with 60 g of a 50/50 (w/w) nickel/aluminum alloy. After stirring for 30 minutes at the same temperature, a solution of 0.128 liters of 100% hydrazine hydrate in 1.28 liters of water was added dropwise in two hours under stirring. Stirring was continued for further 30 minutes then, after adding 80 g of Dicalite ® and bringing the pH to 9 by means of concentrated hydrochloric acid, the whole was filtered. The filtrate was heated to 80° C., brought to pH 3 by means of concentrated hydrochloric acid, cooled to 35° C. whereby the obtained solid was recovered by filtration. After washing with water until neutrality and drying, 1.140 Kg of the title compound were obtained. Yield 98% of theoretical.

$[\alpha]_D^{20} = +67°$(C=1% in CHCl$_3$). M.p. 155°-56° C.

EXAMPLE 8

Following substantially the same procedures of Examples 4-7 the compound d,l-2-(6-methoxy-2-naphthyl)-propionic acid was prepared, starting from d,l-2-(5-bromo-6-methoxy-2-naphthyl)-propionic acid. M.p. 154°-55° C.

The optically resolution for obtaining the d-2-(6-methoxy-2-naphthyl)-propionic acid was performed as described in Italian patent application 3492 A/80. M.p. of the end product: 155° C.; $[\alpha]_D^{20} = +66.3°$(C=1% in CHCl$_3$)

We claim:

1. A process for preparing the d-2-(6-methoxy-2-naphthyl)-propionic acid of formula I

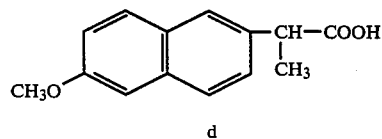

which consists of (1) reacting a mixture of d- and l-2-(5-bromo-6-methoxy-2-naphthyl)-propionic acids of formula II

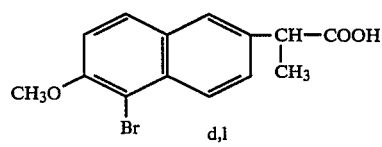

with N-methyl-D-glucamine in a solvent system selected from mixtures of toluene and methanol in various volumetric ratios, in the presence of an optically inactive organic or inorganic base, at a temperature between about room temperature and about 65° C., whereby the N-methyl-D-glucamine salts of the d- and l-isomers of said compound of formula II are formed, letting the less soluble N-methyl-D-glucamine salt of the d-isomer precipitate, separating said salt from the reaction mixture, (2) reacting said salt with a strong mineral acid, whereby the compound d-2-(5-bromo-6-methoxy-2-naphthyl)-propionic acid of formula III

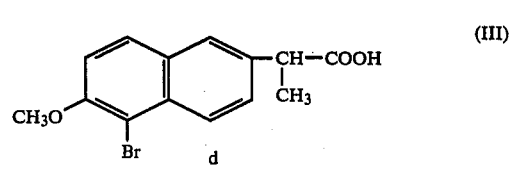

is obtained, and (3) catalytically hydrogenating said compound of formula III in an alkaline medium at a temperature between about room temperature and about 100° C. for a period of time varying from 1 to about 4 hours, whereby the bromine atom in the 5-position is replaced by hydrogen and isolating said compound of formula I from the reaction mixture.

2. A process as defined in claim 1, wherein the mixture of d- and l-2-(5-bromo-6-methoxy-2-naphthyl)-propionic acid is a substantially racemic mixture.

3. A process as defined in claim 2, wherein for each molar amount of the substantially racemic mixture of d- and l-2-(5-bromo-6-methoxy-2-naphthyl)-propionic acids about one half molar porportion of N-methyl-D-glucamine is reacted.

4. A process as defined in claim 1, wherein the mixture of toluene and methanol in said step (1) is a 4/1 or 3/1 (v/v) mixture.

5. A process as defined in claim 1, wherein the temperature in step (1) is from about room temperature to about 55° C.

6. A process as defined in claim 1, wherein said step (3) is carried out by hydrogenation with (a) palladium/-charcoal; (b) palladium/charcoal or platinum dioxide with a mixed metal hydride; (c) a mixture of a mixed metal hydride and a salt of a transition metal; (d) a mixture of Devarda's alloy and a mixed metal hydride; (e) Ni/Raney and hydrazine hydrate; or (f) nickel-/aluminum alloy and hydrazine hydrate.

7. A process as defined in claim 6 wherein the hydrogenation is carried out with palladium/charcoal and sodium borohydride.

8. A process as defined in claim 6, wherein the hydrogenation is carried out with copper sulfate pentahydrate and sodium borohydride.

9. A process as defined in claim 6, wherein the hydrogenation is carried out with Ni/Raney or a 50/50 (by weight) nickel-aluminum alloy, and hydrazine hydrate.

10. A process as defined in claim 1, wherein the hydrogenation is carried out at a temperature between about room temperature and about 50° C. with Ni/-Raney or a nickel/aluminum alloy, and hydrazine hydrate.

11. A process for preparing d-2-(6-methoxy-2-naphthyl)-propionic acid of formula I

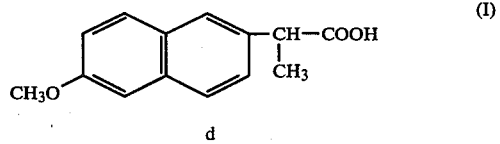

which consists of (1) reacting a molar amount of a substantially racemic mixture of d- and l-2-(5-bromo-6-methoxy-2-naphthyl)-propionic acids of formula

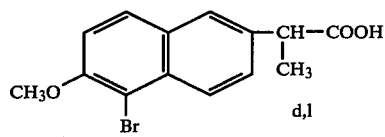

with about one half molar proportion of N-methyl-D-glucamine in the presence of a 4/1 (v/v) toluene/methanol mixture as the reaction solvent, in the presence of about one half molar amount of triethylamine, at a temperature between about room temperature and about 55° C., letting the less soluble N-methyl-D-glucamine salt of the d-isomer precipitate, separating said salt from the reaction mixture, (2) reacting said salt from step (1), with a strong mineral acid, whereby the compound d-2-(5-bromo-6-methoxy-2-naphthyl)-propionic acid of formula III

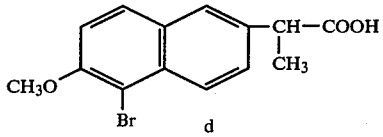

is obtained, and (3) catalytically dehalogenating said compound of formula III by treatment with a hydrogenation system capable of providing a complete replacement of the bromine atom at the 5-position by a hydrogen atom, said hydrogenating system being (1) 5% palladium/charcoal and sodium borohydride, (2) copper sulfate pentahydrate and sodium borohydride, (3) nickel/aluminum alloy and 100% hydrazine hydrate, (4) Ni/Raney and 100% hydrazine hydrate, in an alkaline medium, at a temperature between about room temperature and about 100° C., for a period of time varying from about 1 to about 4 hours and isolating said compound of formula I from the reaction mixture.

12. A process as defined in claim 11, wherein the hydrogenating system is Ni/Raney or 50/50 (by weight) nickel/aluminum alloy, and 100% hydrazine hydrate.

13. The process according to claim 1 or 11 wherein in said step (1) the reaction mixture in said solvent of toluene and methanol mixtures is seeded with the salt of N-methyl-D-glucamine and d-2-(5-bromo-6-methoxy-2-naphthyl)-propionic acid.

14. The N-methyl-D-glucamine salt of d-2-(5-bromo-6-methoxy-2-naphthyl)-propionic acid.

* * * * *

REEXAMINATION CERTIFICATE (734th)
United States Patent [19]
Cannata et al.

[11] B1 4,423,244
[45] Certificate Issued  Jul. 28, 1987

[54] PROCESS FOR THE PREPARATION OF THE D-2-(6-METHOXY-2-NAPHTHYL)-PROPIONIC ACID

[75] Inventors: Vincenzo Cannata, Borgo Nuovo di Pontecchio Marconi; Giancarlo Tamerlani, Pontecchio Marconi, both of Italy

[73] Assignee: Alfa Chemicals Italiana S.p.A., Milan, Italy

Reexamination Request:
No. 90/001,017, May 30, 1986

Reexamination Certificate for:
Patent No.: 4,423,244
Issued: Dec. 27, 1983
Appl. No.: 362,679
Filed: Mar. 29, 1982

[30] Foreign Application Priority Data
Apr. 1, 1981 [IT] Italy .................. 3385 A/81

[51] Int. Cl.$^4$ .................................. C07C 65/105
[52] U.S. Cl. .................. 562/466; 260/501.17
[58] Field of Search ........................... 562/466

[56] References Cited
U.S. PATENT DOCUMENTS

| | | |
|---|---|---|
| 3,683,015 | 8/1972 | Dyson . |
| 3,686,183 | 8/1972 | Dyson .................. 260/284 |
| 3,988,365 | 10/1976 | Gallegra . |
| 3,994,968 | 11/1976 | Alvarez .................. 260/520 D |
| 4,246,164 | 1/1981 | Felder et al. .................. 260/501.17 |
| 4,246,191 | 1/1981 | Holton .................. 260/501.17 |

OTHER PUBLICATIONS

Egli, R., *Helv. Chim Acta,* 51, 2090-2097 (1968) (translation) Fieser & Fieser, "Reagents for Organic Synthesis" vol. I (John Wiley & Sons) 1967, pp. 434-445, 581, 595, 718-720, 890-892.

Fieser & Fieser, "Reagents for Organic Synthesis" vol. VI, (1977), pp. 502-503.

Freifeld, M., "Practical Catalytic Hydrogenation" (Wiley-Interscience 1971), pp. 58-63, 451-452.

House, H. "Modern Synthetic Reactions," Second ed. (W. A. Benjamin, Inc., 1972), pp. 1-14, 247-248.

*Primary Examiner*—Paul J. Killos

[57] ABSTRACT

A new process for the preparation of the d-2-(6-methoxy-2-naphthyl)-propionic acid of formula

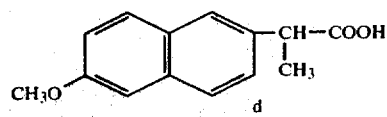

which comprises resolving a racemic mixture of the d- and l-2-(5-halo-6-methoxy-2-naphthyl)-propionic acids of formula

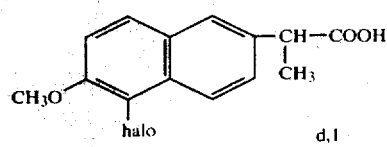

wherein halo stands for a halogen atom, recovering the d-isomer and subjecting this isomer to catalytic dehalogenation. Compound I is obtained in very high yields and with a high purity degree.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 11, 12, 13 and 14 is confirmed.

Claim 2 and 4 are cancelled.

Claim 1 is determined to be patentable as amended.

Claims 3, 5–10 and 13, dependent on an amended claim, are determined to be patentable.

1. A process for preparing the d-2-(6-methoxy-2-naphthyl)-propionic acid of formula I

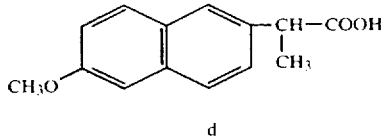

which consists of (1) reacting a mixture of d- and l-2-(5-bromo-6-methoxy-2-naphthyl)-propionic acids of formula II

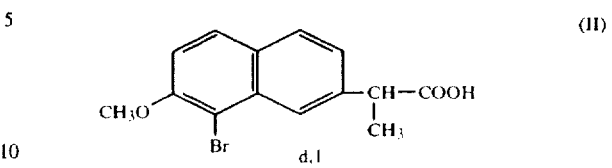

with N-methyl-D-glucamine in a solvent system selected from mixtures of toluene and methanol [in various volumetric ratios.] *wherein the mixture of tolune and methanol in said step (1) is a 4/1 or 3/1 (v/v) mixture*, in the presence of an optically inactive organic or inorganic base, at a temperature between about room temperature and about 65° C., whereby the N-methyl-D-glucamine salts of the d- and l-isomers of said compound of formula II are formed, letting the less soluble N-methyl-D-glucamine salt of the d-isomer precipitate, separating said salt with a strong mineral acid, whereby the compound d-2-(5-bromo-6-methoxy/2-naphthyl)-propionic acid of formula III

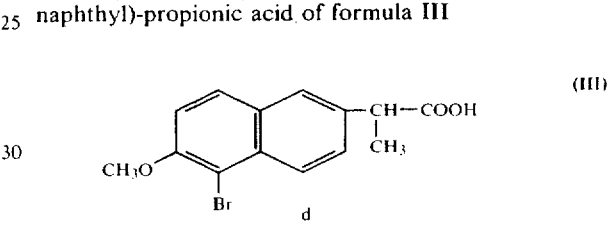

is obtained, and (3) catalytically hydrogenating said compound of formula III in an alkaline medium at a temperature between about room temperature and about 100° C. for a period of time varying from 1 to about 4 hours, whereby the bromine atom in the 5-position is replaced by hydrogen and isolating said compound of formula I from the reaction mixture.

* * * * *